United States Patent
Jacobs et al.

(10) Patent No.: US 7,195,919 B2
(45) Date of Patent: Mar. 27, 2007

(54) HEMATOLOGY CONTROLS FOR RETICULOCYTES AND NUCLEATED RED BLOOD CELLS

(75) Inventors: Dana B. Jacobs, Blue Ridge, VA (US); Paul W. Price, Watkinsville, GA (US); Nery Ortiz, Miami, FL (US); Theodore J. Gerula, Fort Lauderdale, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 304 days.

(21) Appl. No.: 10/741,390

(22) Filed: Dec. 19, 2003

(65) Prior Publication Data

US 2005/0136409 A1    Jun. 23, 2005

(51) Int. Cl.
*G01N 33/554*    (2006.01)
*G01N 31/00*    (2006.01)

(52) U.S. Cl. .................. 436/10; 436/8; 436/66

(58) Field of Classification Search .............. 436/8, 436/10, 66
See application file for complete search history.

(56) References Cited

U.S. PATENT DOCUMENTS

| | | |
|---|---|---|
| 3,873,467 A | 3/1975 | Hunt |
| 4,198,206 A | 4/1980 | Ryan |
| 4,213,876 A | 7/1980 | Crews et al. |
| 4,219,440 A | 8/1980 | Runck et al. |
| 4,264,470 A | 4/1981 | Chastain et al. |
| 4,299,726 A | 11/1981 | Crews et al. |
| 4,358,394 A | 11/1982 | Crews et al. |
| 4,390,632 A | 6/1983 | Carter |
| 4,436,821 A | 3/1984 | Ryan |
| 4,452,773 A * | 6/1984 | Molday ............. 424/1.37 |
| 4,672,040 A * | 6/1987 | Josephson ............ 436/526 |
| 4,704,364 A | 11/1987 | Carver et al. |
| 4,777,139 A | 10/1988 | Wong et al. |
| 4,868,104 A * | 9/1989 | Kurn et al. ............. 435/6 |
| 5,008,021 A | 4/1991 | Conner et al. |
| 5,122,600 A * | 6/1992 | Kawaguchi et al. ....... 536/23.1 |
| 5,125,737 A | 6/1992 | Rodriguez et al. |
| 5,132,242 A * | 7/1992 | Cheung ............. 436/501 |
| 5,262,327 A | 11/1993 | Ryan |
| 5,270,208 A | 12/1993 | Ryan |
| 5,320,964 A | 6/1994 | Young et al. |
| 5,380,489 A * | 1/1995 | Sutton et al. ........... 422/68.1 |
| 5,380,664 A | 1/1995 | Carver et al. |

(Continued)

OTHER PUBLICATIONS

Ebrahim, A., et al., "Encapsulation of Ribonucleic Acid in Human Red Blood Cells for Use as a Reticulocyte Quality Control Material for Flow Cytometric Analysis", *Cytometry*, 25:156-163 (1996).

(Continued)

*Primary Examiner*—Arlen Soderquist
(74) *Attorney, Agent, or Firm*—Cuspa Technology Law Associates; Mitchell E. Alter

(57) ABSTRACT

The present invention is drawn to a hematology control made from particles a particle having a biopolymer attached to a surface of the particle. The particle simulates a component of a blood sample, such as a reticulocyte or nucleated red blood cell component of a blood cell sample in a flow cytometer or hematology analysis instrument. The present invention is further drawn to methods of making and using the hematology control.

21 Claims, 6 Drawing Sheets

U.S. PATENT DOCUMENTS

| | | | |
|---|---|---|---|
| 5,432,089 A | 7/1995 | Ryan et al. | |
| 5,460,797 A | 10/1995 | Ryan | |
| 5,512,485 A | 4/1996 | Young et al. | |
| 5,529,933 A | 6/1996 | Young et al. | |
| 5,559,037 A | 9/1996 | Kim et al. | |
| 5,639,666 A * | 6/1997 | Shenkin | 436/63 |
| 5,648,225 A | 7/1997 | Kim et al. | |
| 5,672,474 A | 9/1997 | Ryan | |
| 5,677,145 A | 10/1997 | Ryan | |
| 5,731,205 A | 3/1998 | Ryan | |
| 5,736,402 A | 4/1998 | Francis et al. | |
| 5,776,754 A * | 7/1998 | Caldwell | 435/325 |
| 5,811,099 A | 9/1998 | Ryan | |
| 5,858,789 A | 1/1999 | Francis et al. | |
| 5,858,790 A | 1/1999 | Kim et al. | |
| 5,874,310 A | 2/1999 | Li et al. | |
| 5,882,863 A * | 3/1999 | Imai et al. | 435/6 |
| 5,917,584 A | 6/1999 | Li et al. | |
| 5,945,340 A | 8/1999 | Francis et al. | |
| 5,972,611 A * | 10/1999 | Furuichi et al. | 435/6 |
| 5,981,282 A | 11/1999 | Ryan | |
| 6,074,879 A * | 6/2000 | Zelmanovic et al. | 436/10 |
| 6,100,038 A * | 8/2000 | Dertinger et al. | 435/6 |
| 6,187,590 B1 | 2/2001 | Kim et al. | |
| 6,200,500 B1 | 3/2001 | Ryan | |
| 6,221,668 B1 | 4/2001 | Ryan et al. | |
| 6,399,388 B1 | 6/2002 | Ryan et al. | |
| 6,403,377 B1 | 6/2002 | Ryan et al. | |
| 6,406,915 B2 | 6/2002 | Ryan et al. | |
| 6,410,330 B1 | 6/2002 | Li et al. | |
| 6,444,471 B1 * | 9/2002 | Johnson | 436/10 |
| 6,448,085 B1 | 9/2002 | Wang et al. | |
| 6,472,215 B1 | 10/2002 | Huo et al. | |
| 6,514,763 B2 | 2/2003 | Carver et al. | |
| 6,569,682 B2 | 5/2003 | Elliott et al. | |
| 6,573,102 B2 | 6/2003 | Li et al. | |
| 6,592,821 B1 * | 7/2003 | Wada et al. | 422/68.1 |
| 6,653,063 B2 | 11/2003 | Carver et al. | |
| 6,653,137 B2 | 11/2003 | Ryan | |
| 6,673,618 B1 | 1/2004 | Li et al. | |
| 6,759,246 B1 * | 7/2004 | Collins | 436/10 |
| 6,933,106 B2 * | 8/2005 | Hechinger | 435/4 |
| 6,962,817 B2 * | 11/2005 | Li et al. | 436/63 |
| 2001/0046708 A1 | 11/2001 | Carver et al. | |
| 2003/0104630 A1 | 6/2003 | Ryan | |

OTHER PUBLICATIONS

Morrison and Boyd, *Organic Chemistry*, 2nd Edition, 1966, Allyn and Bacon, Inc., pp. 879 and 989.

\* cited by examiner

HEMATOLOGY CONTROLS FOR RETICULOCYTES AND NUCLEATED RED BLOOD CELLS

FIELD OF THE INVENTION

The present invention is drawn to hematology controls, their method of manufacture and use, particularly to nucleated red blood cell (NRBC) controls and reticulocyte cell controls that can be incorporated into a hematology control product without interfering with the function of any of the other components and parameters present in said hematology control product.

BACKGROUND OF THE INVENTION

Quality control has long been a necessary and routine procedure in clinical hematology. Accuracy in the counting of various types of blood cells is dependent, in part, upon the use of adequate control products and methods of using the control products. With the numerous types of equipment for particle counting now available, quality control by the use of control products is necessary, since the possibility of instrument malfunctioning is ever present. The traditional method of maintaining a quality control program for automatic particle counting equipment has consisted of providing fresh human blood as a whole blood standard. However, this fresh blood is usable for only one day, therefore, various manufactured control products which have longer product lifetime have been developed.

Commonly used particles in a control product simulate or approximate the types of particles or cells that are intended to undergo analysis. Consequently, these particles have been frequently referred to as analog particles. The analog particles should be selected or designed so that they have certain characteristics that are similar to those of the particles or cells to be analyzed in the instruments. Exemplary characteristics and parameters include similarities in size, volume, surface characteristics, granularity properties, light scattering properties and fluorescence properties.

The current state of the art of automated hematology instruments permits the user to perform a full analysis of the components of a blood sample, i.e. analysis of the hematological parameters. These parameters include, but are not limited to: white blood cell count ("WBC"), neutrophil cell percent or count ("NE %" or "NE#"), lymphocyte cell percent or count ("LY %" or "LY#"), monocyte cell percent or count ("MO %" or "MO#"), eosinophil cell percent or count ("EO %" or "EO#"), basophil cell percent or count ("BA %" or "BA#"), nucleated red blood cell percent or count ("NRBC %" or "NRBC#"), red blood cell count ("RBC"), hemoglobin concentration ("Hgb"), hematocrit ("Hct"), mean corpuscular volume ("MCV"), red blood distribution width ("RDW"), platelet count ("PLT"), mean platelet volume ("MPV"), platelet distribution width ("PDW"), platelet hematocrit ("Pct"), reticulocyte cell percent or count ("RET %" or "RET#"), mean reticulocyte volume ("MRV") and immature reticulocyte fraction ("IRF"). Of no less importance, the functions of the hematology controls, hereinafter sometimes referred to as controls, are to ensure that the hematology analyzer itself and the reagent systems being used are operating within their specified parameters. As hematology analysis systems become more complex and provide for the analysis of additional parameters, that is parameters derived from electrical, optical and/or fluorescence analysis, appropriate controls are needed, which enable the instrument system users to also monitor the performance of these newly available parameters.

Various commercial reference control products are now available, which use various processed or fixed human or animal blood cells as analogs of human blood cells. U.S. Pat. No. 5,512,485 (to Young et al) teaches a hematology control comprising several white blood cell analogs made of processed and fixed animal red blood cells. U.S. Pat. Nos. 6,187,590 and 5,858,790 (to Kim et al) teach a hematology control comprising white blood cell analogs and a nucleated red blood cell (NRBC) analog made of lysed and fixed avian or fish red blood cells. These particles have been developed for fluorescence-based, multi-angle light scatter NRBC detection systems. U.S. Pat. Nos. 6,406,915, 6,403,377, 6,399,388, 6,221,668, and 6,200,500 (to Ryan, et al) teach a hematology control comprising a NRBC analog derived from avian blood cells. U.S. Patent Application Publication Nos. 2003/0104630 (to Ryan) teach methods of making a hematology control containing a nucleated red blood cell component by stabilizing nucleated containing blood cells, or by lysing and removing cytoplasm from blood cells. Ryan's hematology control only triggers NRBC flags on instruments, such as the Beckman Coulter STKS™ and GEN*S™ instruments.

U.S. Pat. No. 6,448,085 (to Wang et al) teaches a hematology control comprising a nucleated red blood cell (NRBC) analog derived from chicken blood and fixed human blood with nucleated red blood cells. However, these types of NRBC analogs, being fixed whole cells, significantly interfere with detection methodologies that are monitored by typical five-part differential hematology control product.

U.S. Pat. No. 5,432,089 teaches a method for preparing a reticulocyte analog by loading nucleic acid into erythrocytes using osmotic lysis techniques. However, the osmotic technology described in U.S. Pat. No. 5,432,089 only yields approximately 20% of the RBC being sufficiently "loaded" with RNA to create a reticulocyte analog. As a result, to create a moderately high level control in the range of 8–10% reticulocytes, the treated material can only be diluted 2 to 2.5 fold, which does not lend itself to an efficient manufacturing process.

Francis, et al. (U.S. Pat. Nos. 5,945,340; 5,858,789; and 5,736,402) teach methods for preparing reticulocyte analogs by arresting the maturation of natural porcine reticulocytes recovered from blood. However, porcine reticulocytes are significantly smaller than human reticulocytes, i.e. they possess a significantly lower MRV, making their reliable detection problematic on some automated hematology analyzers.

In addition, several detection methods for measuring nucleated red blood cells in a blood sample on a hematology instrument have been reported. U.S. Pat. Nos. 5,874,310 and 5,917,584 (to Li et al) generally teach a method of differentiating nucleated red blood cells by measuring two angles of light scatter signals of a blood sample under lysing condition without the requirement of using fluorescence analysis. U.S. Pat. Nos. 5,874,310 and 5,917,584 further teach a method of differentiating nucleated red blood cells by measuring light scatter and DC impedance signals. U.S. Pat. No. 6,410,330 (to Li et al) and co-pending patent application U.S. Ser. No. 10/226,800 (to Li et al) generally provide a method of determining NRBC by using DC impedance measurement.

U.S. Pat. No. 6,472,215 (to Huo et al) teaches a method of differentiating nucleated red blood cells by lysing a first aliquot and a second aliquot of a blood sample separately with a first lysing reagent system and a second lysing reagent system; measuring the first sample mixture in a flow cell by DC impedance, radio frequency, and light scatter measurements; measuring cell distributions and counting remaining blood cells in the second sample mixture by DC impedance measurements in a non-focused flow aperture; analyzing blood cell distribution patterns obtained from measuring the first sample mixture and from measuring the second sample mixture respectively; and further performing a combined analysis to differentiate NRBCs from other cell types and determine numbers of NRBCs in the blood sample.

A material that is useful in a hematology control product possesses several key properties. One important property of the material is that the material interacts with the hematology instrument and reagent system in a manner that is similar to the interaction of the patient blood sample with the hematology instrument and reagent system. In addition, the material provides a consistent and predictable result as long as the hematology analyzer and reagent system are operating within specified parameters. When the hematology analyzer and/or the reagent system are not within specified parameters, then it should be indicated by a control result that is inconsistent with the expected, predictable output. Another desirable property of a hematology control is stability. The parameter values that a user recovers when testing the control by the same method that a clinical sample would be tested, should be sufficiently stable so that the user has confidence in the control's ability to detect instrument malfunctions over a product lifespan that is sufficiently long enough to be considered economical by the user. Still another desirable property is that the method for manufacturing has a high product yield which is greater than 30% and more preferably greater than 40%.

SUMMARY OF THE INVENTION

The present invention is directed to a hematology control comprising a particle having a biopolymer attached to a surface of the particle, said particle simulating a component of a blood sample. In one embodiment, the hematology control comprises a particle having a biopolymer attached to a surface of the particle, said particle simulating a reticulocyte in a blood sample. Similarly, a further embodiment is directed to a hematology control comprising a particle having a biopolymer attached to a surface of the particle, said particle simulating a NRBC in a blood sample. In a further embodiment, the particle comprises a red blood cell, preferably mammalian. In still a further embodiment, the hematology control comprising a human red blood cell having RNA attached to a surface of the cell through cross-linking.

An additional embodiment of the invention is a hematology control that simulates a reticulocyte in an optical-fluorescence based detection instrument and an electrical-optical based detection instrument. Similarly, a further embodiment is directed to a hematology control that simulates an NRBC in an optical-fluorescence based detection instrument and an electrical-optical based detection instrument.

The present invention is further drawn to a method of making a hematology control comprising attaching a biopolymer to a surface of a particle, wherein said particle simulating a component of a blood sample.

Still further, the present invention is drawn to a method of using a hematology control.

BRIEF DESCRIPTION OF THE DRAWINGS

FIG. 5($b$) is a fluorescence microscopic evaluation of the same acridine orange stained analog of Example 5 that is shown in FIG. 5($a$).

DETAILED DESCRIPTION OF THE INVENTION

Figure 1:
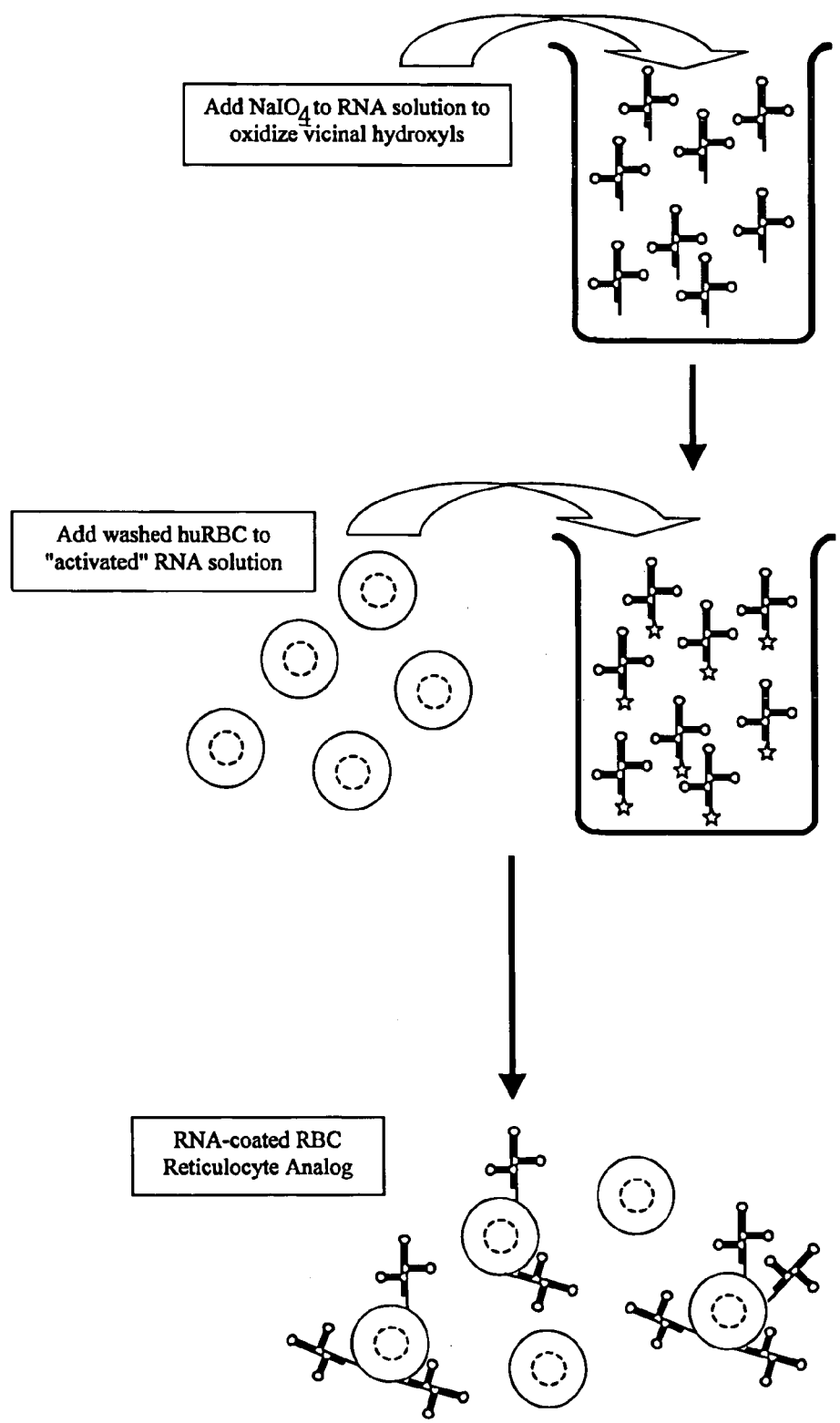
FIG. 1 is a schematic for coating the external surface of washed human RBC with periodate-activated RNA.

The present invention is drawn to hematology controls and their method of manufacture. The hematology controls of the invention are made from particles, which have been coated on their external surface with a biopolymer for use with hematology analyzers and flow cytometers (microfluorimeters). The invention is particularly directed to red blood cells, as a class of particles that have their external surface coated with a biopolymer to create an NRBC control or reticulocyte control for use with hematology analysis instruments or flow cytometers.

The biopolymer used in the present invention can be any synthetic or naturally occurring material that is derived from a desired aspect of a cell or any synthetic or naturally occurring material that is capable of mimicking a desired aspect of a cell and that has the ability to form stable attachments to the external surface of the target particle. Examples of suitable biopolymers include natural and synthetic mucopolysaccharides and nucleic acids (RNA or DNA) and any material that can be stably cross-linked to an appropriate target particle. For the purposes of creating a reticulocyte or NRBC analog, the biopolymer is any compound with which a nucleic acid binding ligand (e.g. a dye) will form a stable complex, including but not limited to DNA, RNA, peptide nucleic acids ("pNA's"), and polymers with suitable ionic or hydrophobic regions that will form sufficiently stable non-covalent complexes with detector ligands, e.g. dyes. RNA is well suited for this invention because ribonucleic acids are complex polymeric carbohydrates that are, for the design of this invention, unique in that there is only one monosaccharide unit at the three prime (3') end of the molecule that exhibits vicinal hydroxyl groups.

The biopolymer can be attached to the particle using either covalent or ionic cross-linking, with covalent cross-linking being preferred. Routine cross-linking chemistry can be used to covalently bind the biopolymer to the external surface of the particle. If the biopolymer is a nucleic acid-based biopolymer, then suitable hetero- and homo-bifunctional chemical cross-linkers are those that will react with the amino groups of the individual nucleotide bases (such as those on adenine, guanine, and cytosine) on one end and with a reactive moiety (such as an amino, carboxy or sulfhydryl group) found on the target cell surface (for example, within a protein, lipoprotein, lipid or sugar) on the other end. Suitable bifunctional chemical cross-linkers are described in Means, G. E. and Feeney, R. E., Chemical Modification of Proteins, 1971, Holden-Day, Inc. or the Pierce Chemical catalogue (Pierce Endogen, Rockford, Ill.). Examples of suitable cross-linking agents include amine to sulfhydryl, amino to carboxy and amine to amine linkers. Amine to sulfhydryl linkers include N-β-maleimidopropionic acid and maleimidobenzoyl-N-hydroxysulfosuccinimate. Amine to carboxy linkers include ethyl dimethylaminopropyl carbodimide (EDAC). Amine to amine linkers include glutaraldehyde, di(adenine dialdehyde) triphosphate (DAD-TP), and dimethyl adipimidate, ethylene glycobis (sulfosuccinimidylsuccinate).

In another embodiment, if the biopolymer is RNA or an RNA-based polymer, then the RNA can be linked to the particle surface after oxidation of the 3'-OH (i.e. vicinal hydroxyl) groups to form aldehydes. Oxidation of vicinal hydroxyl group with periodate, for example, is well known in the art (Organic Chemistry, Morrison and Boyd, 2nd Edition, 1966, Allyn and Bacon, Inc., pages 879, 989). The use of periodate to oxidize vicinal hydroxyl groups contained within complex carbohydrate or monosaccharides, such as agarose or glucose to form reactive aldehydes for the purpose of coupling a ligand to the reactive aldehyde are also well known.

The biopolymer can be obtained from either synthetic or naturally occurring sources. If RNA is used as the biopolymer, convenient sources include bakers' yeast and Torula yeast. Generally, the RNA may be dissolved in a suitable buffered solution, e.g. acetate or borate buffered solution, at RNA concentrations over the range of approximately 0.5% to 20% (w/v), and preferably 1% to 10% (w/v), with the dissolution reaction dependent upon the solubility of RNA in the buffered solution at temperature ranges from approximately 1° C. to 100° C., preferably 10° C. to 60° C., and most preferably 18° C. to 40° C., and pH ranges from 1 to 14, preferably 4 to 12, and most preferably 8 to 10. The dissolved RNA is reacted at a temperature between approximately 10° C. and 60° C., and preferably between 18° C. to 30° C., with a periodate salt such as sodium periodate, potassium periodate, or tetrabutyl ammonium periodate at periodate ion concentrations ranging from approximately 0.125 mM to 200 mM, and preferably from 0.25 mM to 5 mM, over a pH range of 2 to 12, preferably 4.0 to 6.0. Unconsumed periodate ion may be further reacted with a molar excess of a simple glycol, such as glycerol. The formic acid and any residual periodate are removed by dialysis, diafiltration, desalting chromatography or other similar means known to those skilled in the art using an iso-osmotic buffered solution in the pH range of 2 to 12, preferably 4.0 to 6.0. The reaction generates an RNA preparation with activated aldehydes at the 3' ends of the RNA strands that are available to react with amines and alcohols. Primary amines, which are more reactive with aldehydes than alcohols (hydroxyls), are abundantly available in proteins and amino sugars on the surface of invertebrate and vertebrate cells, including mammalian red blood cells, and can be used to cross-link the RNA to the cell surface. The reaction between the aldehyde and amine forms a Schiff base, which may be reduced to form secondary or tertiary amines, which are more stable than the unreduced Schiff base. Suitable reducing agents, which are known to those skilled in the art, include, but are not limited to beta-mercaptoethanol, ascorbate, and sodium cyanoborohydride.

The particles used in the present invention can be derived from any suitable natural or synthetic material that meets the criteria of being able to be stably coated with the biopolymer and being representative of a normal component of a hematology sample when analyzed using a modern day hematology analyzer or by flow cytometry. Preferably, the particles, when so coated can be integrated into a multiparametric hematology control product without interfering with any other control analogs so integrated. Preferred particles for use in the present invention are mammalian red blood cells. However, avian, reptilian, or porcine RBC can be used when the desired analog requires coating with cell type-specific biopolymers. An example of this would be to create a basophil analog by coating an alligator RBC with molecules found in basophil granules, such as mucopolysaccharides and arachidonic acid metabolites (including products of the lipoxygenase and cyclooxygenase pathways). Additionally, particles made from polystyrene, latex or other synthetic material, as well as amino dextrans, can be coated using appropriately modified chemical cross-linkers.

Red blood cells can be obtained from mammalian blood, including bovine, elephant, goat, horse, or human blood, using well-known, standard procedures. For example, mammalian blood that has been anti-coagulated with ethylenediaminetetraacetic acid ("EDTA"), citrate phosphate dextrose adenine ("CPDA-1") or acid citrate dextrose ("ACD") can be washed with an iso-osmotic buffered saline to remove the buffy coat, platelets and plasma. The red blood cells can be suspended at a concentration in the range of approximately $0.5–4.0 \times 10^6$ cells/μL in the same iso-osmotic saline used for dialysis or diafiltration of the activated nucleic acid (DNA or RNA). To compensate for the buffering capacity of hemoglobin, small quantities of the conjugate acid of the buffer can be added as required to maintain the desired pH in the range of approximately 4.0 to approximately 6.0.

For electrical, optical and/or fluorescence based detection systems, the present invention is based upon major attributes possessed by nucleated red blood cells and reticulocytes. Those attributes are a) a volume of approximately 50–65 fL for the NRBC, and 95–120 fL for the reticulocyte; b) contains nucleic acids (DNA or RNA or both), and c) contains hemoglobin. In one embodiment, the invention is comprised of mammalian red blood cells of which the external surface has been coated by covalent or ionic attachment of a nucleic acid (DNA or RNA) or a material with which a nucleic acid binding ligand (e.g. a dye) will form a stable complex.

In an embodiment wherein the particle is desired to function as a reticulocyte analog, the suitable mammalian red blood cells have an MCV about equal or greater than the normal MCV of a human RBC. In this embodiment, suitable sources include, but are not limited to human RBC (MCV approximately 85–95 fL, elephant RBC (MCV approximately 120–125 fL), and cetacean (MCV approximately 115–125 fL).

In an embodiment wherein the particle is desired to function as a NRBC analog, the suitable mammalian RBC have an MCV significantly less than a normal human RBC for detection in instruments such as the Beckman Coulter STKS and GEN*S, that utilize a VCS detection system which is a non-fluorescence based systems. Preferably, the particle MCV is less than 70 fL. Suitable sources include, but are not limited to, porcine RBC (MCV approximately 50–65 fL), equine RBC (MCV approximately 35–50 fL), bovine RBC (MCV approximately 35–50 fL), and bovine RBC (MCV approximately 30–40 fL), with equine RBC being preferred.

As a result, the particles can be detected as NRBC or reticulocytes in electro-optical based system such as a VCS system, optical-fluorescence based system such as in flow cytometry (microfluorimetry) system, as well as an optical based system and electrical-optical-fluorescence based system that may or may not rely on nucleic acid binding ligands (dyes) for identifying the reticulocyte or NRBC. Such ligands are well-known to those skilled in the art, and include fluorescent (acridine orange, propidium iodide, ethidium bromide, cyanine dyes) and non-fluorescent dyes (new methylene blue, Coomassie brilliant blue).

Equal volumes of activated RNA and washed RBCs are mixed together, and the coupling reaction is allowed to proceed with continuous gentle mixing at room temperature for a period of time sufficient for completion of said reaction. The preferred reaction time is from at least 10 minutes to approximately 24 hours, preferably from about 20 minutes to approximately 18 hours, and most preferably from 1 to 5 hours. If reduction of the Schiff base is desired, a molar excess of a suitable reducing agent, e.g. beta-mercaptoethanol or sodium cyanoborohydride is added to the coupling mixture and the reaction is allowed to proceed from 20 minutes to 1 hour at room temperature, a standard time interval understood by those skilled in the art. A diagrammatic representation of the periodate coating of RBCs with RNA is presented in FIG. 1.

Alternatively, RNA or other nucleic acid-based biopolymers may be cross-linked to the external surface of RBCs using a bifunctional cross-linking agent. For example, RNA, from a convenient source such as bakers' yeast or Torula yeast, is dissolved in a suitable buffered solution, e.g. borate, carbonate, phosphate, etc., at RNA concentrations over the range of approximately 0.5% to 20% (w/v), and preferably 1% to 10% (w/v), with the dissolution reaction dependent upon the solubility of RNA in the buffered solution at temperature ranges from approximately 1° C. to 100° C., preferably 10° C. to 60° C., and most preferably 18° C. to 40° C., and pH ranges from 1 to 14, preferably 4 to 12, and most preferably 9 to 11. The dissolved RNA is reacted with the cross-linking reagent at an elevated temperature that is sufficient to modify the secondary and tertiary structure of the RNA so as to make the amino groups of the nucleotide bases available for reaction with the cross-linking reagent. RNA typically begins to denature at approximately 45° C., with denaturation occurring rapidly at approximately 60° C. If DNA is used as a biopolymer, DNA typically begins to denature at approximately 70° C. or greater, with the optimal temperature of denaturation being dependent on the AT:GC content. The methods for determining the optimum ratio of RNA and cross-linking reagent is well known to those familiar with the art. Unconsumed cross-linking agent may be removed by dialysis, diafiltration, or precipitation of the nucleic acid with cold ethanol.

Figure 2:
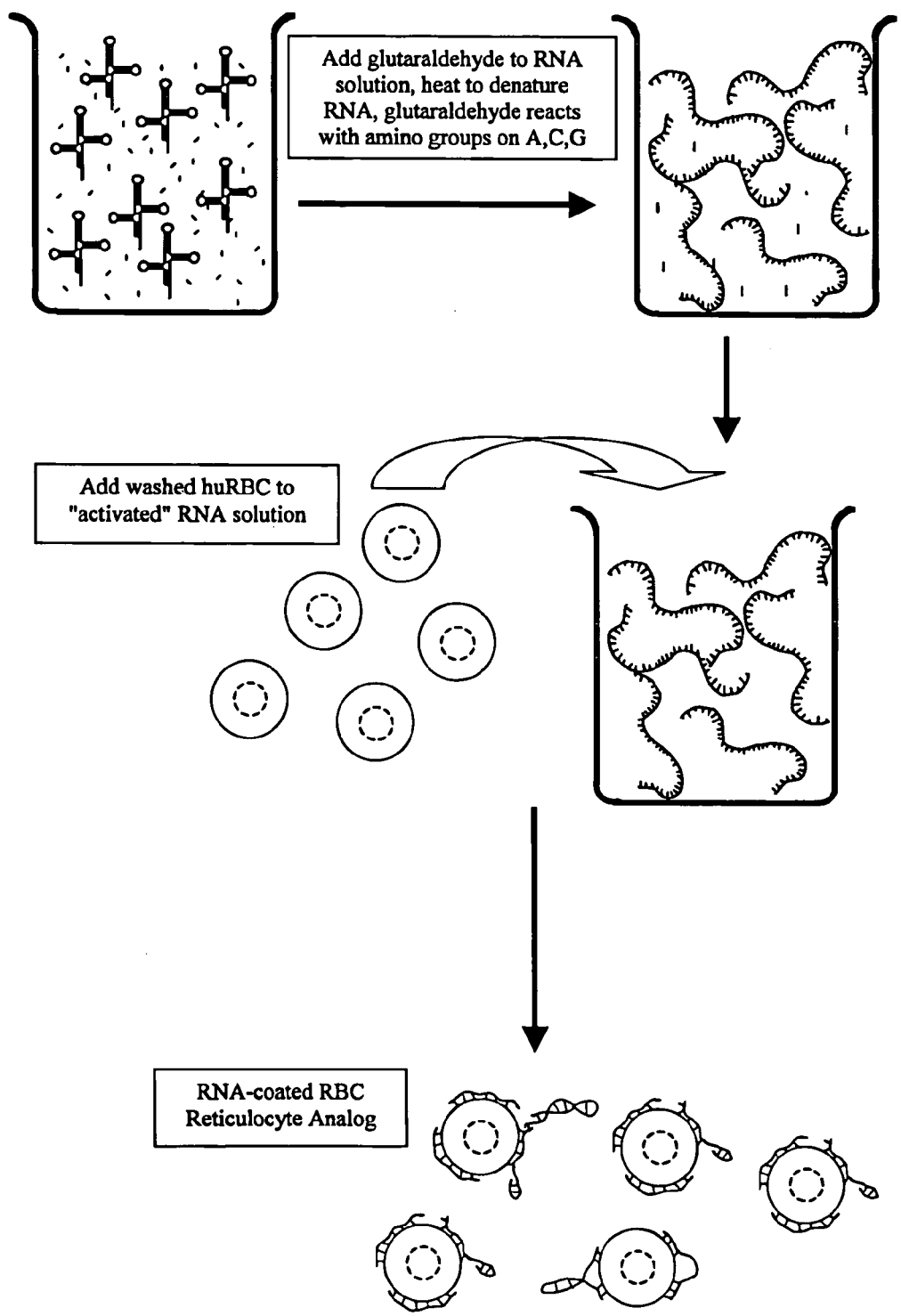
FIG. 2 is a schematic for coating the external surface of washed mammalian RBC with glutaraldehyde-activated RNA.

To coat the RNA on the surface of the RBCs, volumes of activated RNA and washed RBCs are mixed together such that preferably saturation of RBC surface proteins by RNA is approached to provide a very useful control, and the coupling reaction is allowed to proceed with continuous gentle mixing at room temperature for a period of time sufficient for completion of said reaction. The preferred reaction time is from at least approximately 10 minutes to approximately 24 hours, preferably from 20 minutes to 18 hours, and most preferably from 1 to 5 hours. If reduction of the Schiff base is desired, a molar excess of a suitable reducing agent, e.g. beta-mercaptoethanol, ascorbate, or sodium cyanoborohydride is added to the coupling mixture and the reaction is allowed to proceed, as necessary. For example, if sodium cyanoborohydride is used the reaction may permitted to proceed for from approximately 20 minutes to approximately 1 hour at room temperature. If, on the other hand, beta-mercaptoethanol or ascorbate are used, which are not as harsh, the reaction may proceed overnight at approximately 2° C. to approximately 8° C. A diagrammatic representation of glutaraldehyde-mediated cross-linking of RNA to RBCs is presented in FIG. 2.

In yet another embodiment, RBCs may also be surface coated with biopolymer indirectly by first cross-linking the biopolymer to a second biopolymer (e.g. a protein), and linking that compound to RBCs. In one such example, RNA is covalently linked with, for example, glutaraldehyde using a process described above. Avidin is then dissolved in an appropriate phosphate, borate, or carbonate buffer at pH in the range of 1 to 14, preferably 6 to 12, and most preferably 8.0 to 10.5. The glutaraldehyde-activated RNA is added to the avidin at approximately 1.5 to 4-fold molar excess, and allowed to react for a period of time sufficient for completion of said reaction. The preferred reaction time is from at least approximately 10 minutes to approximately 24 hours, preferably from 20 minutes to 18 hours, and most preferably from 1 to 5 hours. If reduction of the Schiff base is desired, a molar excess of a suitable reducing agent, e.g. beta-mercaptoethanol, ascorbate, or sodium cyanoborohydride is added to the coupling mixture and the reaction is allowed to proceed from approximately 20 minutes to approximately 1 hour at room temperature. Un-reacted RNA may be separated from the RNA-avidin complex by means of chromatography, dialysis or diafiltration by methods known to those skilled in the art. As a further part of this example, biotin N-hydroxysuccinimide ester (BNHS, biotin) is dissolved at an appropriate concentration (approximately to 50 mg/ml) in an appropriate volume of N,N dimethylformamide. The mammalian RBCs are washed as described above and re-suspended in borate buffered saline (approximately 270 to approximately 310 mOsm, pH approximately 8.5 to approximately 9) to a concentration of approximately 0.5 to $4.0 \times 10^6$ cells/mL. Biotin is added in an amount of approximately 20 μl per $1.0 \times 10^6$ cells and the suspension is incubated with gentle stirring at room temperature for and allowed to react for a period of time sufficient for completion of said reaction. The preferred reaction time is from at least approximately 10 minutes to approximately 24 hours, preferably from 20 minutes to 18 hours, and most preferably from 90 min to 4 hours. Un-reacted biotin may be removed by washing the cell suspension with iso-osmotic saline. To coat the RNA on the surface of the RBCs, volumes of avidin-RNA and biotinylated RBCs are mixed together such that preferably saturation of RBC surface proteins by RNA is approached to provide a very useful control, and the coupling reaction is allowed to proceed with continuous gentle mixing at room temperature for approximately 120 minutes to approximately 18 hours (overnight).

In a similar embodiment, both the biopolymer and the RBC may be linked to biotin and the cross-linking mediated through avidin. Still another embodiment utilizes covalent binding of activated biopolymer to an antibody molecule that has been raised against a surface protein specific to the mammalian RBC, such as glycophorin-A, band-3, or Rh antigens. The antibody-biopolymer conjugate may then be coupled to RBC at a concentration such that preferably saturation of the protein is approached to provide a very useful control, and the coupling reaction allowed to proceed with continuous gentle mixing at room temperature for a period of time from approximately 120 minutes to approximately 18 hours.

Once the control is manufactured, it is suspended in a suitable stabilizing suspension medium for storage and use on an analyzer. Suitable examples of the suspension media are well known to those skilled in the art and preferably include those medias disclosed in U.S. Pat. No. 6,569,682 to Elliott et al. and U.S. Pat. No. 5,529,933 to Young et al. which are hereby incorporated by reference in their entirety. These media may contain other ingredients known to those skilled in the art to confer long term stability. Other examples of suitable media are more fully described in U.S. Pat. Nos. 4,213,876, 4,299,726, 4,358,394, 3,873,467, 4,704,364, 5,320,964 and 5,512,485, which are herein incorporated by reference in their entirety.

Of particular interest with the present invention are controls for reticulocytes and NRBC that can be measured on a modern hematology analyzer, such as those that utilize Beckman Coulter VCS technology, which is more fully described in U.S. Pat. No. 5,125,737 to Rodriguez et al.; electrical and optical based systems as more fully described in U.S. Pat. Nos. 5,874,310; 5,917,584; 6,410,330 (to Li et al) and/or in classical flow cytometry (microfluorimetry). Such controls have been problematic in the past because while they may function well within one platform, their ability to serve as controls with the other platform has been unsatisfactory. For example, the current Beckman Coulter, Inc. Retic-C™ reticulocyte hematology control performs admirably within the confines of VCS technology. However, since the Retic-C control consists of an avian (nucleated) RBC and therefore possesses significant DNA, it is "too bright" and therefore unsuitable for accepted flow cytometry reticulocyte methods that rely on detection of cytoplasmic RNA using fluorescent nucleic acid dyes. Similarly, the reticulocyte analog taught in U.S. Pat. No. 5,432,089, while providing a suitable control for flow cytometry-based applications, has proved to be unsuitable with newer hematology analyzers due to markedly low MRV. In addition, previously some, but not all, reticulocyte and NRBC controls have been problematic in the past because of interference with other controls, particularly the five part differential parameters.

In addition, the hematology control contemplates the addition of a white blood cell component which simulates at least three, and preferably five subpopulations of white blood cells. The hematology control further contemplates the addition of other blood components to resemble corresponding components in whole blood such as platelets and stabilized red blood cells that provide red blood cell parameters, such as count, MCV and RDW.

In different embodiments, the blood cell components may be derived from a source that will exhibit the size, shape or other measurable characteristics of human, animal, or other whole blood. By way of non limiting examples, U.S. Pat. Nos. 3,873,467; 4,198,206; 4,219,440; 4,264,470; 4,299,726; 4,358,394; 4,436,821; 4,390,632; 4,704,364; 4,777,139; 5,008,021; 5,262,327; 5,270,208; 5,320,964; 5,380,664; 5,432,089; 5,460,797; 5,512,485; 5,672,474; 5,677,145; 5,731,205; 5,811,099; 5,981,282; 6,200,500; and 6,221,668, which are each hereby incorporated by reference, each contain examples of these types of blood cell components.

EXEMPLIFIED EMBODIMENTS OF THE INVENTION

Example 1

RNA Activation by Oxidation with 0.001M Sodium Periodate and Coupling to Human Erythrocytes Bakers' yeast RNA is dissolved at 1% (w/v) in 0.05M sodium acetate buffer, pH 4.6. Sufficient solid sodium periodate is added to achieve 0.001M sodium periodate. The reaction is allowed to proceed at room temperature for approximately one hour. A volume of glycerol approximately equal to 1/100th of the reaction volume is added to consume any remaining periodate, and this consumption reaction is allowed to proceed for approximately 10–15 minutes. The reaction mixture is transferred to a prepared dialysis sac and dialyzed against three, ten-fold changes of 0.05M buffered acetate saline, pH 5.0. The dialyzed activated RNA is removed from the sac and stored refrigerated.

Human blood that has been anti-coagulated with EDTA, CPDA-1 or ACD is washed with an iso-osmotic buffered saline, as is well known to those familiar with the art, to remove the buffy coat, platelets and plasma. The red blood cells are then suspended at a concentration in the range of approximately $2.0 \times 10^6$ cells/µL in the same iso-osmotic saline used for dialysis of the periodate oxidized activated RNA. To compensate for the buffering capacity of hemoglobin, small quantities of acetic acid are added as required to maintain the cell suspension within the desired pH in the range of approximately 5.0–5.5.

Equal volumes of periodate oxidized activated RNA and washed RBCs are mixed together, and the coupling reaction is allowed to proceed with continuous gentle mixing at room temperature for approximately 18 hours. Reduction of the Schiff base is accomplished by the addition of a volume of 0.01M sodium cyanoborohydride equal to 5% of the coupling reaction volume, and the reduction reaction is allowed to proceed for 1 hour at room temperature.

Figure 3:
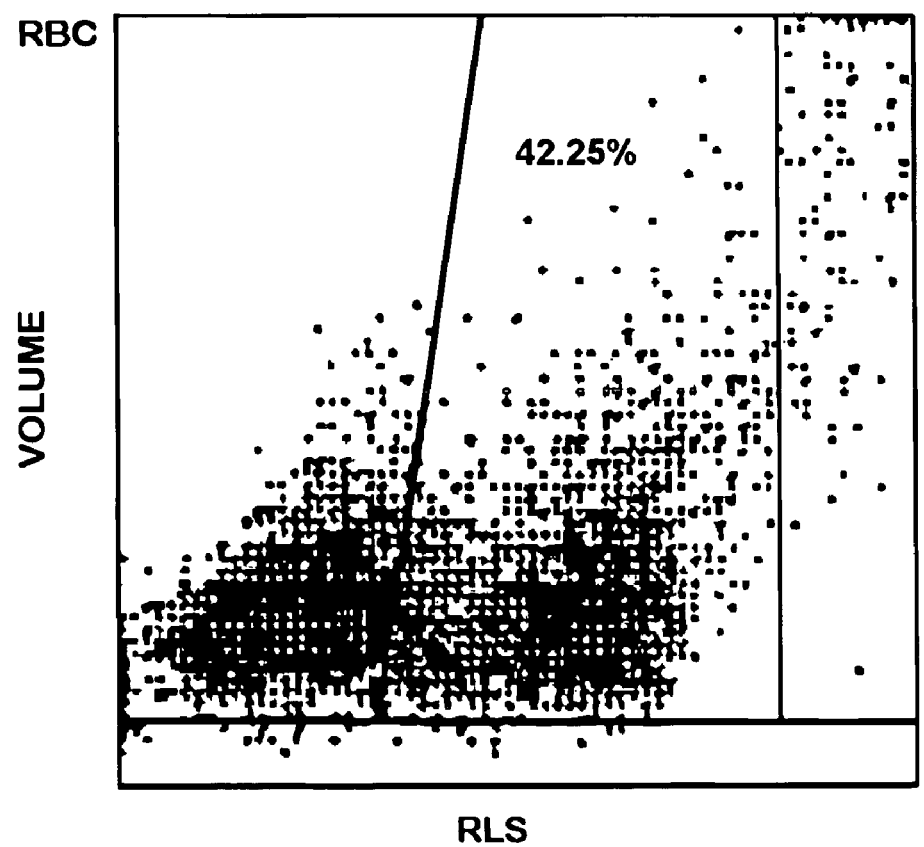
FIG. 3 is an analysis of reticulocyte analogs of Example 1 using a Beckman Coulter STKS instrument, demonstrating a reticulocyte recovery of 42%.
Figure 4:
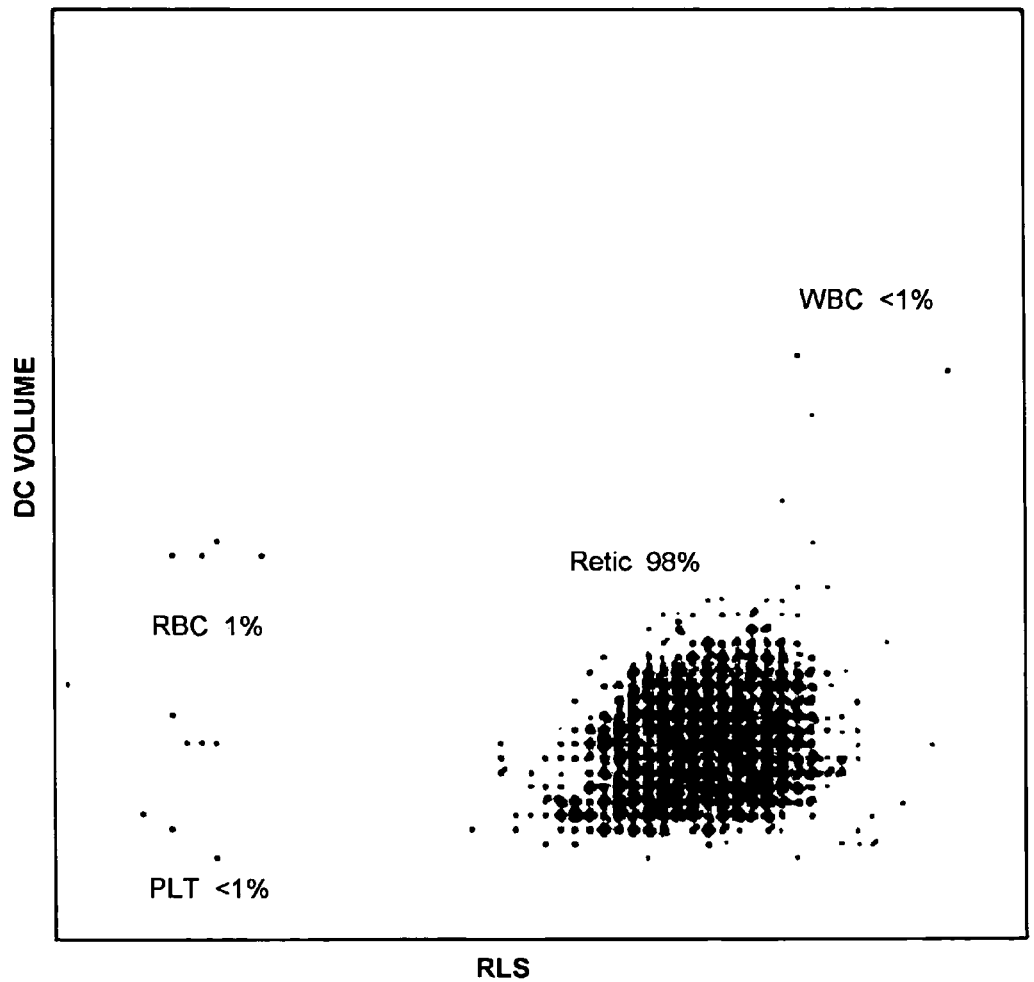
FIG. 4 is an analysis of reticulocyte analogs prepared according to Example 4 using a Beckman Coulter LH 750 instrument, demonstrating >98% reticulocytes as a stand-alone product.

The RNA coated RBCs are washed by repeated centrifugation and resuspension in buffered saline as is well known in the art and stored refrigerated in saline or a suitable storage media. Analysis of the analog on a Beckman Coulter STKS™ demonstrating a reticulocyte recovery of 42% is illustrated in FIG. 3.

Example 2

RNA Activation by Oxidation with 0.2M Sodium Periodate and Coupling to Human Erythrocytes Bakers' yeast RNA is dissolved at 1% (w/v) in 0.05M sodium acetate buffer, pH 4.6. Sufficient solid sodium periodate is added to achieve 0.2M sodium periodate. The reaction is allowed to proceed at room temperature for approximately one hour. A volume of glycerol approximately equal to 1/100th of the reaction volume is added to consume any remaining periodate, and this consumption reaction is allowed to proceed for approximately 10–15 minutes. The reaction mixture is transferred to a prepared dialysis sac and dialyzed against three ten-fold changes of 0.05M buffered acetate saline, pH 5.0. The dialyzed activated RNA is removed from the sac and stored refrigerated.

Human blood that has been anti-coagulated with EDTA, CPDA-1 or ACD is washed with an iso-osmotic buffered saline, as is well known to those familiar with the art, to remove the buffy coat, platelets and plasma. The red blood cells are then suspended at a concentration in the range of approximately 2.0×106 cells/µL in the same iso-osmotic saline used for dialysis of the periodate oxidized activated RNA. To compensate for the buffering capacity of hemoglobin, small quantities of acetic acid are added as required to maintain the cell suspension within the desired pH in the range of 5.0–5.5.

Equal volumes of periodate oxidized activated RNA and washed RBCs are mixed together, and the coupling reaction is allowed to proceed with continuous gentle mixing at room temperature for approximately 18 hours. Reduction of the Schiff base is accomplished by the addition of a volume of 0.01M sodium cyanoborohydride equal to 5% of the coupling reaction volume, and the reduction reaction is allowed to proceed for 1 hour at room temperature.

The RNA coated RBCs are washed by repeated centrifugation and resuspension in buffered saline as is well known in the art and stored refrigerated in saline or a suitable storage media. Analysis of the analog on a Beckman Coulter STKS demonstrated a reticulocyte recovery of approximately 60%.

Example 3

Reticulocyte Control with Beckman Coulter 5C Abnormal II Cell Control Product

A typical reticulocyte control that is currently available is the Beckman Coulter Retic-C Cell control, which is a non-integrated control that utilizes avian red blood cells to simulate human reticulocytes. Material made according to the process described in Example 1 was spiked into Beckman Coulter 5C® Abn II Cell Control Product and the results obtained are shown in Table 1.

TABLE 1

Results of spiking Retic analog from Example 1 into 5C Abn II Cell Control Product.

| Parameter | 5C Abn II Cell control | 5C Abn II Cell control spiked with analogs from example #1 |
|---|---|---|
| Ret % | 0.36 | 3.58 |
| RBC | $1.88 * 10^6/\mu l$ | $1.82 * 10^6/\mu l$ |
| WBC | $3.3 * 10^6/\mu l$ | $3.7 * 10^6/\mu l$ |
| NE % | 44.1 | 42.2 |
| LY % | 45.4 | 42.5 |
| MO % | 6.4 | 8.5 |
| EO % | 3.8 | 6.6 |
| BA % | 0.3 | 0.2 |

Example 4

RNA Activation by Coupling with Glutaraldehyde and Subsequent Coating of Human Erythrocytes Bakers' yeast RNA is dissolved at 5% (w/v) in 0.1M sodium borate buffer, pH 10. Sufficient glutaraldehyde (25% solution) is added to achieve a molar excess of glutaraldehyde over RNA, and the pH adjusted to a range of approximately 4.5 to 6.0, preferably 4.9 to 5.1. The reaction is allowed to proceed at 60° C.±2° C. for approximately two hours. The reaction mixture is then cooled to room temperature, and excess, un-reacted glutaraldehyde is removed by precipitating the RNA-glut using 100% ethanol, as is well known in the art. The precipitate of activated RNA is re-dissolved in 0.1M sodium borate buffer, pH 10 and stored refrigerated.

Human blood that has been anti-coagulated with EDTA, CPDA or ACD is washed with an iso-osmotic buffered saline to remove the buffy coat, platelets and plasma; and the red blood cells are suspended at a concentration in the range of approximately $2.0 \times 10^6$ cells/µL in the same iso-osmotic saline used for washing the cells.

Volumes of glutaraldehyde-activated RNA and washed RBCs are mixed together at a ratio of 0.5 to 1.5 ng RNA per erythrocyte, and the coupling reaction is allowed to proceed with continuous gentle mixing at room temperature for two hours. The RNA-coated cells are then washed by repeated centrifugation and resuspension with an iso-osmotic buffered saline as is well known in the art and resuspended in Dulbecco's Modified Eagle's Medium ("DMEM"). Reduction of the Schiff base is accomplished by the addition of ascorbate to 350 µM, and the reduction reaction is allowed to proceed approximately 18 hours at 4° C.

The RNA coated RBCs are washed by repeated centrifugation and resuspension in buffered saline and stored refrigerated in DMEM or a suitable storage media such as phosphate buffered saline solution and an aqueous solution of a plasma substance. As defined herein, an aqueous solution of a plasma protein. As further defined herein, plasma protein comprises one or more of the proteins contained in plasma. Preferably, such plasma proteins comprise albumin, lipoproteins, globulins, fibrinogens and mixtures thereof. These media may contain other ingredients known to those skilled in the art to confer long term stability. Other examples of suitable media are more fully described in U.S. Pat. Nos. 4,213,876, 4,299,726, 4,358,394, 3,873, 467, 4,704,364, 5,320,964 and 5,512,485, which are herein incorporated by reference in their entirety.

Example 5

RNA Activation by Coupling with Glutaraldehyde and Subsequent Coating of Human Erythrocytes Bakers' yeast RNA is dissolved at 5% (w/v) in 0.1M sodium borate buffer, pH 10. Sufficient glutaraldehyde (25% solution) is added to 0.02% (v/v) of RNA, and pH adjusted to a range of approximately 4.5 to 6.0, preferably 4.9 to 5.1. The reaction is allowed to proceed at 60° C. for approximately two hours. The reaction mixture is then cooled to room temperature, and excess, un-reacted glutaraldehyde is removed by diafiltration against four volumes of 0.1M sodium borate buffer, pH 10 and stored refrigerated or frozen.

Human blood that has been anti-coagulated with EDTA, CPDA-1 or ACD is washed with an iso-osmotic buffered saline to remove the buffy coat, platelets and plasma; and the red blood cells are suspended at a concentration in the range of approximately $2.0 \times 10^6$ cells/µL in the same iso-osmotic saline used for washing the cells.

Volumes of glutaraldehyde-activated RNA and washed RBCs are mixed together at a ratio of 0.5 ng RNA per erythrocyte, and the coupling reaction is allowed to proceed with continuous gentle mixing at room temperature for two hours. The RNA-coated cells are then washed by repeated centrifugation and resuspension with an iso-osmotic buffered saline as is well known in the art and resuspended in DMEM. Reduction of the Schiff base is accomplished by the addition of ascorbate to 350 µM, and the reduction reaction is allowed to proceed approximately 18 hours at 4° C.

Figure 5A:
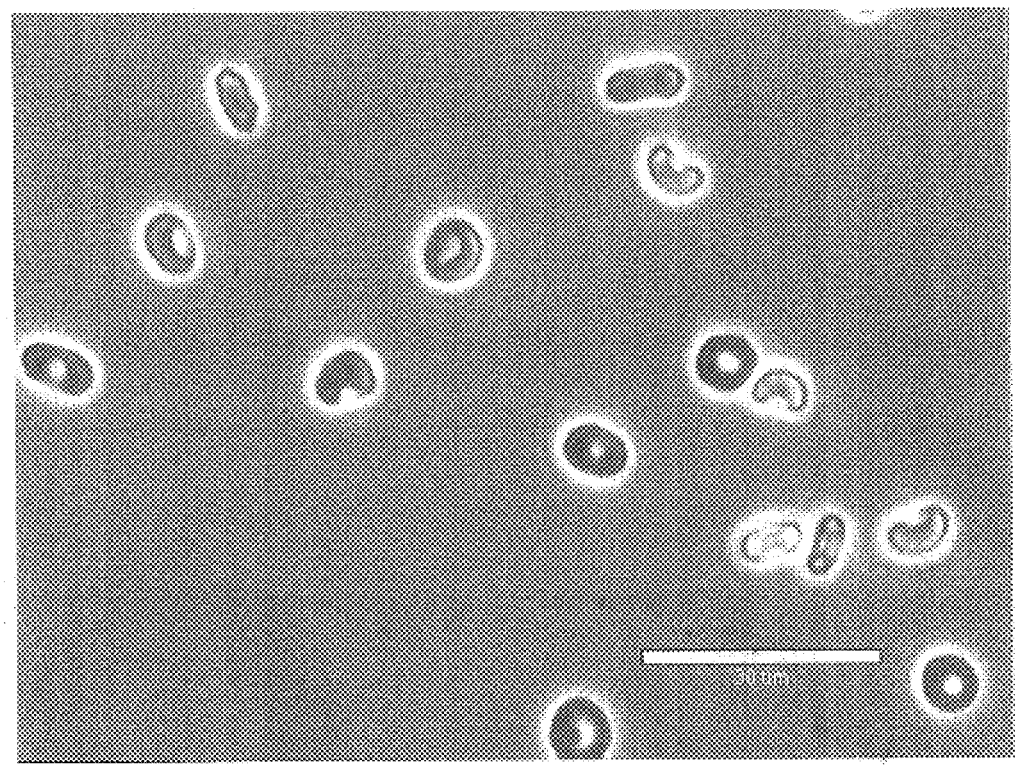
FIG. 5($a$) is a microscopic evaluation of acridine orange stained analog of Example 5 using a bright field.

The RNA coated RBCs are washed by repeated centrifugation and resuspension in buffered saline as is well known in the art and stored refrigerated in DMEM or a suitable storage media. Microscopic evaluation of acridine orange stained analog is illustrated in FIG. 5(a). Analysis of the reticulocyte analog on a Beckman Coulter GEN*S showed a 73% recovery of reticulocytes.

Example 6

Reticulocyte Control with 5C Normal Cell Control Product

The material made according to the process described in Example 4 was spiked into Beckman Coulter 5C Normal Cell control product. Analysis with a prototype Beckman Coulter LH 750 hematology instrument showed approximately 6% reticulocytes. Significant interference with the white blood cell count and leukocyte five-part differential was noted. As a result, this material would be suitable for a non-integrated reticulocyte control rather than inclusion into a multi-parametric control product.

Example 7

Reticulocyte Control with 5C ES Abnormal II Cell Control Product

Material made according to the process described in Example 5 was spiked into Beckman Coulter 5C ES Abnormal II Cell control product and analyzed on a Beckman Coulter Gen*S/LH 750 prototype instrument. At the level shown (approximately 11.5% reticulocytes) there is minimal interference with the leukocyte five-part differential. There is no significant interference with the five-part differential parameters. As such, this material would be suitable for an integrated reticulocyte control product.

Example 8

RNA Activation by Coupling with Glutaraldehyde and Subsequent Coating of Human Erythrocytes Bakers' yeast RNA is dissolved at 5% (w/v) in 0.1M sodium borate buffer, pH 10. Sufficient glutaraldehyde (25% solution) is added to 0.1% (v/v) of RNA, and pH adjusted to a range of approximately 4.5 to 6.0, preferably 4.9 to 5.1. The reaction is allowed to proceed at 60° C. for approximately two hours. The reaction mixture is then cooled to room temperature, and excess, un-reacted glutaraldehyde is removed by diafiltration against four volumes of 0.1M sodium borate buffer, pH 10 and stored refrigerated or frozen.

Human blood that has been anti-coagulated with EDTA, CPDA-1 or ACD is washed with an iso-osmotic buffered saline as is well known to those familiar with the art to remove the buffy coat, platelets and plasma. The red blood cells are then suspended at a concentration in the range of approximately $2.0 \times 10^6$ cells/μL in the same iso-osmotic saline used for washing the cells.

Volumes of glutaraldehyde-activated RNA and washed RBCs are mixed together such at a ratio of 0.5 ng RNA per erythrocyte, and the coupling reaction is allowed to proceed with continuous gentle mixing at room temperature for two hours. The RNA-coated cells are then washed by repeated centrifugation and resuspension with an iso-osmotic buffered saline as is well known in the art and resuspended in DMEM. Reduction of the Schiff base is accomplished by the addition of ascorbate to 350 μM, and the reduction reaction is allowed to proceed approximately 18 hours at 4° C.

Figure 5B:
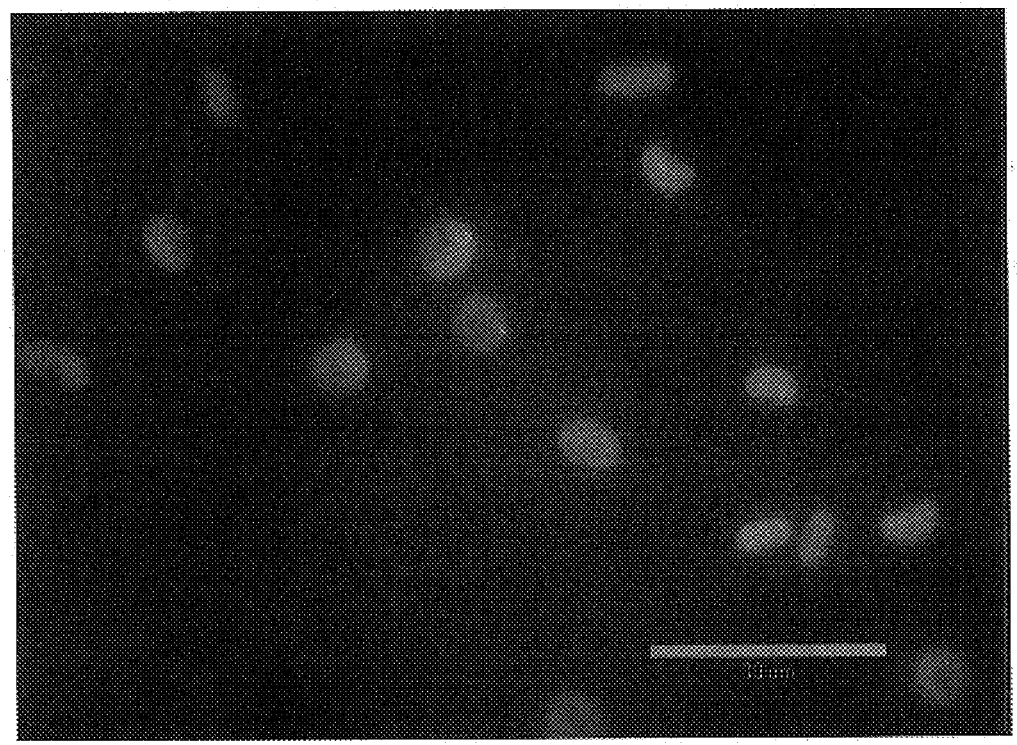

The RNA coated RBCs are washed by repeated centrifugation and resuspension in buffered saline as is well known in the art and stored refrigerated in DMEM or a suitable storage media. Fluorescence microscopic evaluation of acridine orange stained RNA-coated analogs is illustrated in FIG. 5(b). Analysis of the washed control cells and the reticulocyte analog of the invention on a Beckman Coulter prototype instrument using VCS analysis showed respective recoveries of 19% and 99.4% reticulocytes.

Example 9

RNA Activation by Coupling with Glutaraldehyde and Subsequent Coating of Horse Erythrocytes Bakers' yeast RNA is dissolved at 5% (w/v) in 0.1M sodium borate buffer, pH 10. Sufficient glutaraldehyde (25% solution) is added to achieve a molar excess of glutaraldehyde over RNA, and pH adjusted to a range of approximately 4.5 to 6.0, preferably 4.9 to 5.1. The reaction is allowed to proceed at 60° C. for approximately two hours. The reaction mixture is then cooled to room temperature, and excess, un-reacted glutaraldehyde is removed by precipitating the RNA-glutaraldehyde using 100% ethanol as is well known in the art. The precipitate of activated RNA is re-dissolved in 0.1M sodium borate buffer, pH 10 and stored refrigerated.

Mammalian blood that has been anti-coagulated with citrate is washed with an iso-osmotic buffered saline as is well known to those familiar with the art to remove the buffy coat, platelets and plasma. The red blood cells are then suspended at a concentration in the range of approximately $12.0 \times 10^6$ cells/μL in the same iso-osmotic saline used for washing the cells.

Washed RBCs are added to a solution of 25 mg/ml of glutaraldehyde-activated RNA and a ratio of 1.0 ng RNA per erythrocyte, and the coupling reaction is allowed to proceed with continuous gentle mixing at room temperature for two hours. The RNA-coated cells are then washed by repeated centrifugation and resuspension and stored with an iso-osmotic buffered saline DMEM. Reduction of the Schiff base is accomplished by the addition of ascorbate to 350 μM.

Example 10

RNA Activation by Coupling with Glutaraldehyde and Subsequent Coating of Horse Erythrocytes Bakers' yeast RNA is dissolved at 5% (w/v) in 0.1M sodium borate buffer, pH 10. Sufficient glutaraldehyde (25% solution) is added to achieve a molar excess of glutaraldehyde over RNA, and pH adjusted to a range of approximately 4.5 to 6.0, preferably 4.9 to 5.1. The reaction is allowed to proceed at 60° C. for approximately two hours. The reaction mixture is then cooled to room temperature, and excess, un-reacted glutaraldehyde is removed by precipitating the RNA-glutaraldehyde using 100% ethanol as is well known in the art. The precipitate of activated RNA is re-dissolved in 0.1M sodium borate buffer, pH 10 and stored refrigerated.

Horse blood that has been anti-coagulated with citrate is washed with an iso-osmotic buffered saline to remove the buffy coat, platelets and plasma. The red blood cells are then suspended at a concentration in the range of approximately 2.5×10⁶ cells/μL in the same iso-osmotic saline used for washing the cells.

Washed RBCs are added to a solution of 25 mg/ml of glutaraldehyde-activated RNA and a ratio of 1.0 ng RNA per erythrocyte, and the coupling reaction is allowed to proceed with continuous gentle mixing at room temperature for two hours. The RNA-coated cells are then washed by repeated centrifugation and resuspension with an iso-osmotic buffered saline, and finally resuspended in DMEM. Reduction of the Schiff base is accomplished by the addition of ascorbate to 350 μM.

The WBC count with the 5C ES Abnormal II Cell Control product alone was 3.4, while the WBC count when the control was spiked with the NRBC analog was 7.2 due to the higher level of NRBC analog. However, the WBC differential percent results are essentially unchanged. In addition to appearing to the left of the WBC peak in the WBC histogram, the NRBC analogs are also detected at very low DC and mid-range RLS (rotated light scatter) in DF1 view of the five part differential scatterplot.

Example 11

NRBC Control with a 5C ES Abnormal II Cell Control Product

Figure 6:
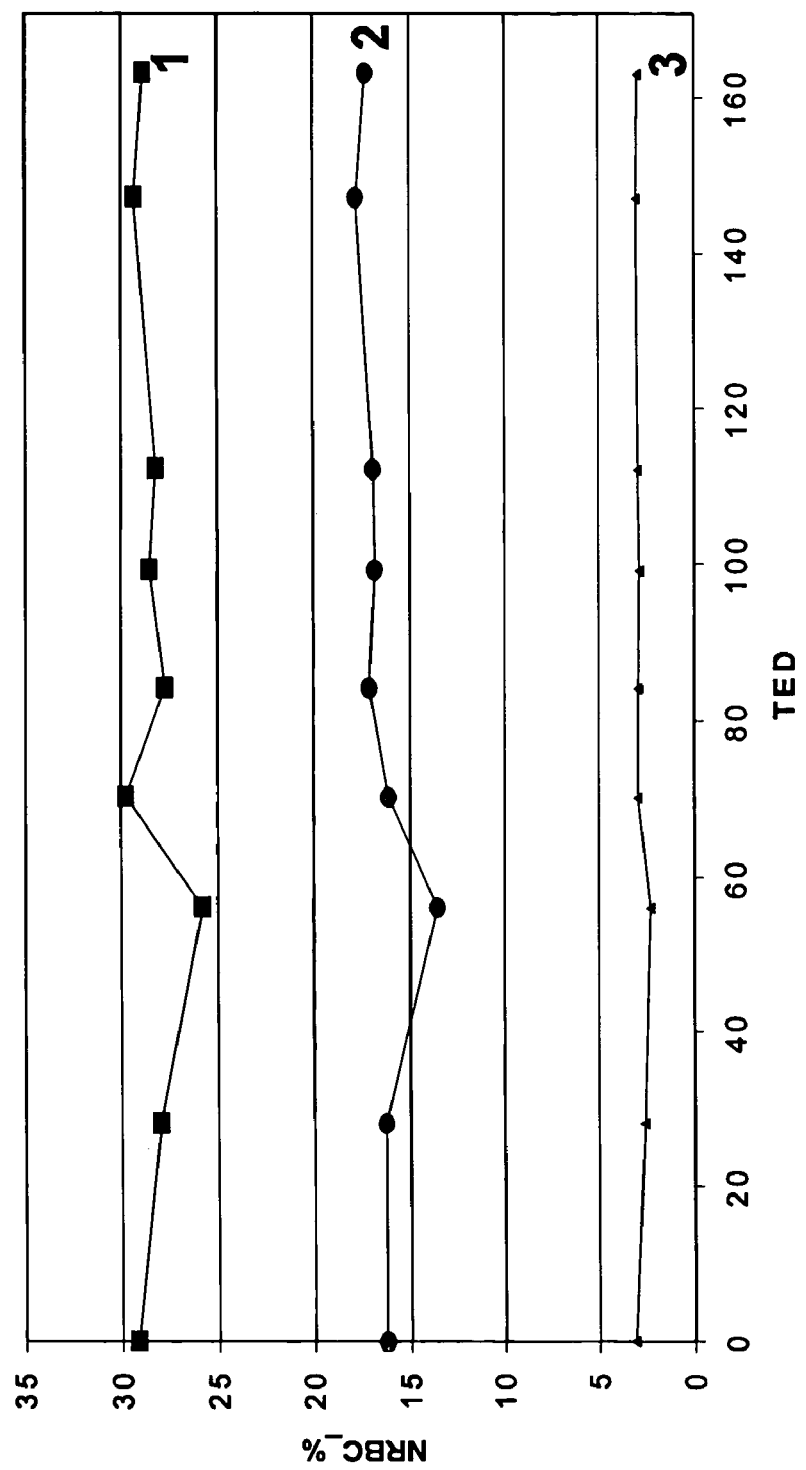
FIG. 6 depicts NRBC analog stability. NRBC analogs were prepared according to the present invention, Example 10, and integrated into a hematology control product that includes white blood cell analogs according to the method of Example 11. Plot 1 shows analogs added to permit recovery of 30 NRBC per 100 WBC; Plot 2 shows analogs added to permit recovery of 15 NRBC per 100 WBC; Plot 3 shows a hematology cell control with no added NRBC, but expressing a debris background of 2–3% of WBC inherent in the hematology control product. Data were collected on a Beckman Coulter instrument using Volume/Conductivity/Light Scatter ("VCS") and DC impedance detection parameters.

The prior art for NRBC analogs utilizes fixed avian erythrocytes (Streck Laboratories, Inc.) to generate NRBC flags on "VCS" instruments or fixed nuclei from avian or piscine porcine erythrocytes or mammalian leukocytes (Abbott Laboratories) to generate NRBC analogs compatible with optical and fluorescent detectors. These types of NRBC analogs are unsuitable for use when integrated into a standard five-part control, such as the Beckman Coulter 5C/5C ES Cell Control Product, because they have a tendency to interfere with the five-part differential measured in the triple transducer module ("TTM") of the VCS detection systems. Materials made per the process described in Examples 9 and 10 were spiked into Beckman Coulter 5C ES Abnormal II Cell control product and analyzed on a Beckman Coulter LH 750 pilot instrument. The stability profile for NRBC analogs incorporated into the 5C ES product at concentrations of approximately 15% and 30% of the WBC count is illustrated in FIG. 6. The results indicated greater than 150 days of closed container stability.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and patent applications cited herein are hereby incorporated by reference in their entirety.

The invention claimed is:

1. A hematology control comprising a biopolymer-coated red blood cell obtained by binding a biopolymer to an external surface of a red blood cell, said biopolymer comprising a nucleic acid, a peptide nucleic acid, or a mucopolysaccharide, and said biopolymer-coated red blood cell simulating a component of a blood sample.

2. The hematology control of claim 1, wherein the biopolymer-coated red blood cell simulates a human reticulocyte.

3. The hematology control of claim 1, wherein the biopolymer is a nucleic acid.

4. The hematology control of claim 3, wherein the nucleic acid is DNA or RNA.

5. The hematology control of claim 1, wherein the red blood cell is a mammalian red blood cell.

6. The hematology control of claim 1, wherein the red blood cell is a human red blood cell.

7. A hematology control comprising a RNA-coated human red blood cell obtained by binding ribonucleic acids to an external surface of a human red blood cell.

8. A hematology control comprising a biopolymer-coated blood cell obtained by binding a biopolymer to an external surface of a blood cell, said biopolymer comprising a nucleic acid, a peptide nucleic acid, or a mucopolysaccharide, and said biopolymer-coated blood cell simulating a reticulocyte in a blood sample.

9. The hematology control of claim 8, wherein the biopolymer-coated blood cell simulates a reticulocyte when measured by optical and fluorescence measurements, or measured by impedance and optical measurements.

10. The hematology control of claim 8, wherein the a blood cell is a mammalian red blood cell.

11. A hematology control comprising a biopolymer-coated particle obtained by binding a biopolymer to an external surface of a particle, said biopolymer comprising a nucleic acid, a peptide nucleic acid, or a mucopolysaccharide, and said biopolymer-coated particle simulating a nucleated red blood cell (NRBC), wherein the particle is a porcine, equine or bovine red blood cell.

12. The hematology control of claim 11, wherein said biopolymer-coated particle simulates a nucleated red blood cell (NRBC) when measured by optical and fluorescence measurements, or measured by impedance and optical measurements.

13. The hematology control of claim 11, wherein the particle has a volume of less than 70 fL.

14. A hematology control comprising a biopolymer-coated red blood cell obtained by covalently binding a biopolymer to an external surface of a red blood cell, said biopolymer enabling forming a complex with a nucleic acid binding dye for simulating a blood cell containing nucleic acids.

15. The hematology control of claim 14, wherein the biopolymer is a nucleic acid or peptide nucleic acid.

16. The hematology control of claim 15, wherein the biopolymer is a nucleic acid.

17. The hematology control of claim 16, wherein the nucleic acid is DNA or RNA.

18. The hematology control of claim 14, wherein the biopolymer is a mucopolysaccharide.

19. The hematology control of claim 14, wherein the red blood cell is a mammalian red blood cell.

20. The hematology control of claim 14, wherein the red blood cell is a human red blood cell.

21. The hematology control of claim 14, wherein the blood cell containing nucleic acids is a reticulocyte or a nucleated red blood cell.

* * * * *